United States Patent [19]

Larson et al.

[11] Patent Number: 5,302,758

[45] Date of Patent: Apr. 12, 1994

[54] DEUTERATED DIBUTYL AND MONOBUTYL PHOSPHATES

[75] Inventors: Richard I. Larson, Wilmington, N.C.; Woodfin V. Ligon, Schenectady, N.Y.; Richard L. Fox, Wilmington, N.C.; Hans Grade, Schenectady, N.Y.

[73] Assignee: General Electric Company, San Jose, Calif.

[21] Appl. No.: 58,180

[22] Filed: May 10, 1993

[51] Int. Cl.$^5$ ............................................. C07F 9/11
[52] U.S. Cl. ................................................. 558/208
[58] Field of Search ....................................... 558/208

[56] References Cited

PUBLICATIONS

Science and Technology of Tributyl Phosphate, vol. I, Synthesis, Properties, Reactions and Analysis, Schulz et al., (ed.), CRC Press, Inc., Boca Raton, Fla., pp. 268, 269, 276, 278, 280–283, 320, 321 (1984).

*Primary Examiner*—Mary C. Lee
*Assistant Examiner*—M. G. Ambrose
*Attorney, Agent, or Firm*—J. S. Beulick

[57] ABSTRACT

An improved internal standard for use in determining the concentration of decomposition products of tributyl phosphate in solvent used for solvent extraction. The improved internal standard includes deuterated variants of the decomposition products to be measured, e.g., deuterated dibutyl and monobutyl phosphoric acids. The use of deuterated dibutyl and monobutyl phosphoric acids eliminates the use of diazomethane, which is toxic and explosive, thereby providing a safer laboratory technique for routine analyses required to monitor production solvent extraction processes.

2 Claims, 3 Drawing Sheets

DEUTERATED DIBUTYL AND MONOBUTYL PHOSPHATES

FIELD OF THE INVENTION

This invention relates to compounds which are useful as internal standards in gas chromatography/mass spectrometry for determining the concentrations of related compounds in a solvent. In particular, it relates to compounds which are useful in determining the concentrations of decomposition products of tributyl phosphate formed during a solvent extraction process for recovering uranium from waste or spent material.

BACKGROUND OF THE INVENTION

The solvent extraction process for recovering uranium consists of a sequence of chemical steps or operations performed on scrap material or spent fuel. First, the scrap material or spent fuel containing uranium compounds is treated with an aqueous solution of nitric acid ($HNO_3$), whereby by the uranium is dissolved to produce uranyl nitrate ($UO_2(NO_3)_2$) and other acid-soluble components in an aqueous phase. This aqueous phase is passed down a solvent extraction column while an organic phase of tri-n-butyl phosphate ("TBP") in an organic diluent of a paraffinic mixture, such as dodecane, is passed up through the extraction column in counter-current flow with the aqueous phase. The soluble uranium compounds of the aqueous phase are extracted therefrom by the organic phase and combined with t-e TBP. The uranium is thus separated from the acid-soluble raffinate contaminants remaining in the aqueous phase and carried by the organic phase from the extraction column. The aqueous and organic phases exit at opposite ends of the extraction column.

The organic phase effluent from the extraction column is then passed up through a stripping column while water is passed down through the stripping column in countercurrent flow with the organic phase. The water releases the uranium from the TBP of the organic phase, whereby it is transferred to and carried within the aqueous phase. The aqueous and organic phases exit at opposite ends of the stripping column, the aqueous phase containing the recovered uranium compounds separated from contaminants. The organic phase is then recycled back through the extraction column. Typically the procedure is carried out With a continuous flow of all components through the system comprising the extraction and stripping columns. The desired product of the solvent extraction process is a high-purity aqueous phase effluent containing virtually all the uranium of the initial waste fed into the system.

Ionizing radiation, elevated temperature and acids cause decomposition of TBP in all of the solvent extraction processes that separate heavy metals, such as uranium, plutonium, thorium and gadolinium. The decomposition products prevent separation of the desired products uranium and plutonium from unwanted wastes, such as gadolinium, zirconium, and fission products.

The acid feed to solvent extraction includes deesterification (dealkylation and hydrolysis) reactions producing dibutyl phosphoric acid (DBP), monobutyl phosphoric acid (MBP), phosphoric acid and butyl alcohol. The sequence of deesterification reactions are summarized below:

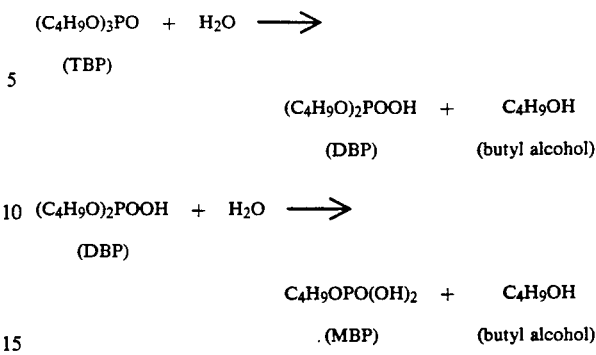

Dibutyl phosphoric acid (DBP) complexes with uranium, zirconium, and gadoliniru, forming compounds soluble in TBP and its solution in hydrocarbon diluents (dodecane or kerosene). This results in a lower gadolinium or zirconium decontamination factor, and an increase in uranium losses in the raffinate, or aqueous waste, produced by the solvent extraction process.

Gas chromatography is the standard analytical method for determining the small quantities of DBP and MBP in TBP and TBP-diluent solutions. To measure these degradation products, DBP and MBP are converted to the more volatile methyl esters, namely, $CH_3DBP$ and $(CH_3)_2MBP$.

Methylation prevents the problems of migration of the low-volatility acids through the packed columns of the gas chromatograph and of their dissociation within the columns. The methylating agent commonly used is diazomethane ($CH_2N_2$), which is both explosive and toxic.

SUMMARY OF THE INVENTION

The present invention is an improved internal standard for use in determining the concentration of decomposition products of tributyl phosphate in solvent used for solvent extraction. The improved internal standard includes deuterated variants of the decomposition products to be measured, e.g., deuterated dibutyl and monobutyl phosphoric acids. The use of deuterated dibutyl and monobutyl phosphoric acids eliminates the use of diazomethane, which is toxic and explosive, thereby providing a safer laboratory technique for routine analyses required to monitor production solvent extraction processes.

The deuterated compounds of the invention can be used as internal standards in gas chromatography/mass spectrometry (GC/MS). The solvent sample to be analyzed is spiked with mass-labelled, deuterated dibutyl and monobutyl phosphates. After adding a silylating agent, bistrimethylsilyltrifluoracetamide (BSTFA), the sample is injected into a gas chromatograph/mass spectrometer, which measures the ratio between the labelled internal standard and the naturally occurring material to obtain a quantitative result. The concentration of the decomposition product of interest is determined using this quantitative result and a calibration curve.

The method of the invention can be used to manufacture deuterated dibutyl phosphoric acid (d-DBP) and deuterated monobutyl phosphoric acid (d-MBP). The first step in the synthesis of the deuterated internal standard is to combine deuterated butanol ($C_4D_9OH$) with phosphorus oxychloride ($POCl_3$) in methylene chloride ($CH_2Cl_2$) and pyridine. The deuterated butanol reacts with phosphorus oxychloride and water to produce d-MBP and d-DBP.

DETAILED DESCRIPTION OF THE PREFERRED EMBODIMENTS

The deuterated compounds in accordance with the invention are used as mass-labelled internal standards for measuring the amount of decomposition products of TBP which are present in a solvent. Deuterated dibutyl and monobutyl phosphates are added to the sample of TBP-dodecane being measured. Both the deuterated and undeuterated dibutyl and monobutyl phosphoric acids are then extracted with water, eliminating most of the TBP and dodecane. After drying, the solid residue is treated with a silylating agent, e.g., BSTFA. This mixture is then analyzed using gas chromatography/mass spectrometry (GC/MS).

Treatment with BSTFA converts the acid phosphates into trimethylsilyl esters, according to the following reactions:

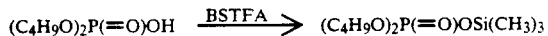

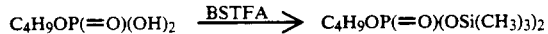

Figure 1:
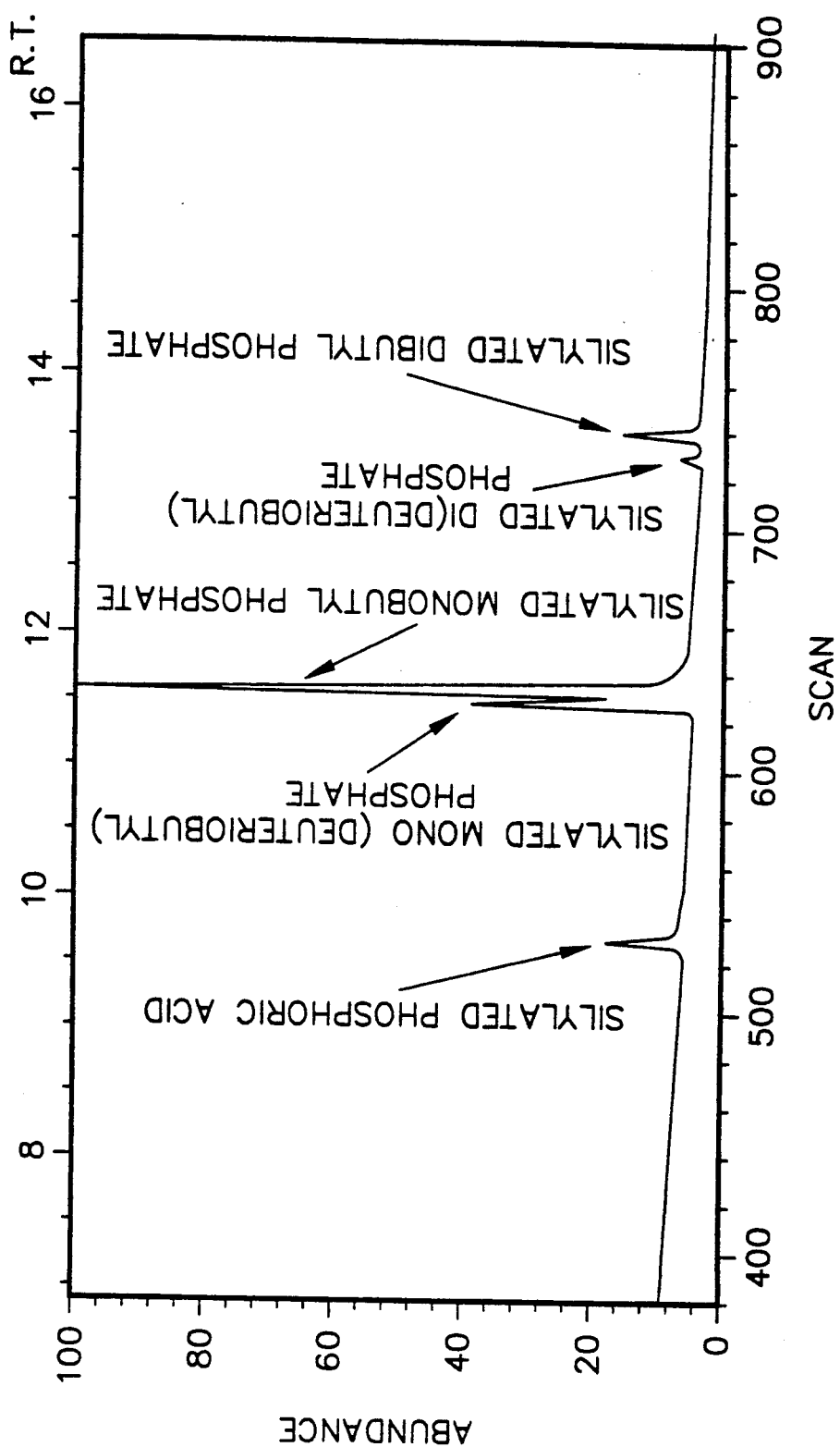
FIG. 1 shows an exemplary chromatogram of a sample of the derivatized solution in accordance with the method of the invention.
Figure 2:
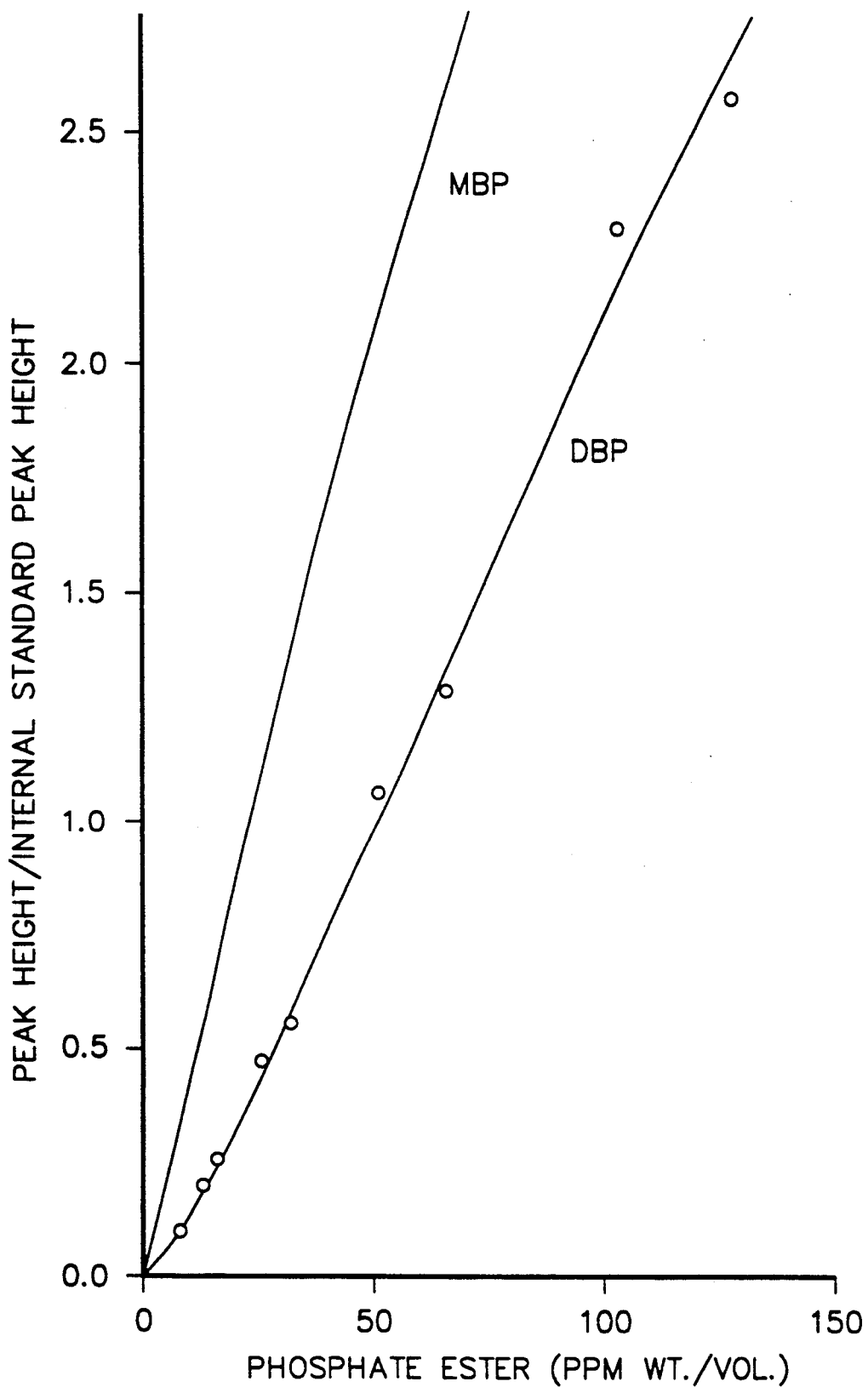
FIG. 2 is a graph showing an empirical calibration plot for the analysis of dibutyl phosphoric acid and a computed calibration plot for monobutyl phosphoric acid analysis in accordance with the method of the invention.

Aliquots of the derivatized solutions are then injected into the gas chromatograph/mass spectrometer. FIG. 1 shows an example of the chromatogram obtained on these samples. FIG. 2 shows a typical butyl phosphate ester analysis calibration plot and the corresponding data points: (□) data; (+) linear regression; and (O) rerun.

The above-described analytical technique requires a deuterated internal standard which must be synthesized. The first step in the synthesis of the deuterated internal standard in accordance with the invention is to combine deuterated butanol ($C_4D_9OH$) with phosphorus oxychloride ($POCl_3$) in methylene chloride ($CH_2Cl_2$) and pyridine. The deuterated butanol reacts with phosphorus oxychloride and water to produce deuterated MBP (d-MBP), deuterated DBP (d-DBP) and deuterated TBP in accordance with the following reaction:

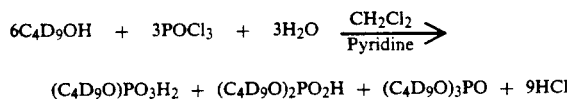

$(C_4D_9O)PO_3H_2 + (C_4D_9O)_2PO_2H + (C_4D_9O)_3PO + 9HCl$

The reactants were combined in a small separatory funnel in the following order: (1) 12.5 ml methylene chloride; (2) 625 μl deuterated butanol; (3) 1900 μl pyridine; and (4) 625 μl phosphorus oxychloride added using a 1-ml syringe. This combination was swirled and then allowed to stand for 10 min.

In accordance with the method of the invention, the reaction was worked up using the following steps in the order indicated: (1) add 12.5 ml of water; (2) insert a stopper in the separatory funnel and shake the funnel vigorously for 2–3 min, being sure to relieve the pressure inside the funnel frequently; (3) allow the layers in the separatory funnel to separate; (4) carefully separate the methylene chloride (bottom) layer; (5) add 12.5 ml of fresh methylene chloride to the separatory funnel and again shake the funnel vigorously; (6) again allow the layers in the separatory funnel to separate; (7) again separate the methylene chloride (bottom) layer and combine it with the first bottom layer; (8) evaporate the combined bottom layers to dryness using a slow stream of dry nitrogen gas; (9) treat the residue from step (8) with 50 ml of diethyl ether (Note: Only part of the residue will dissolve.); (10) decant the ether solution and then treat the residue with a second 50 ml of diethyl ether; (11) decant the second ether solution and combine it with the first ether solution; and (12) evaporate the combined ether solutions to dryness using a stream of dry nitrogen gas.

The d-MBP and d-DBP resulting from this procedure can be used to measure the amounts of MBP and DBP in a TBP or TBP diluent solution. The method of preparing the tributyl phosphate samples for GC/MS analysis comprises the following steps:

(1) Ten microliters of an internal standard solution having a d-DBP concentration of 7.5 μg/μl and a d-MBP concentration of 9.8 μg/μl are injected into a 1-ml conical vial.

(2) The solvent from the internal standard solution (methylene chloride) is evaporated with nitrogen.

(3) One hundred and fifty microliters of water are added to the conical vial and mixed thoroughly for 30 sec using a vortex mixer.

(4) About 350 mg of TBP sample are weighed into the vial and the resulting two-phase solution is agitated with a vortex mixer for 1.5 min.

(5) A syringe is used to transfer the aqueous (bottom) layer to a second conical vial. Care must be taken that the top layer is not sampled.

(6) About 0.5 ml of hexane is added to the second vial containing the aqueous layer and this two-phase system is agitated for 30 sec with a vortex mixer.

(7) A syringe is used to transfer the aqueous (bottom) layer to a third vial.

(8) The water is removed from the third vial using a slow stream of dry nitrogen gas.

(9) After drying, 100 μl of BSTFA is added from an ampule to the dry residue produced by step (8). This mixture is allowed to stand for 30 min at room temperature before analysis.

(10) The solution resulting from step (9) is analyzed by GC/MS using a J&W Scientific model DB-1 capillary column isothermal at 90° C. for 1.5 min and then programmed to rise in temperature from 90° C. to 270° C. at a rate of 8° C./min. The temperature of the injector port was 195° C. The mass spectra were acquired as shown in FIG. 1 and were quantified using the calibration plot shown in FIG. 2.

Although 350 mg of TBP were used in the above example, the amount of TBP is dependent on the sensitivity of the gas chromatograph/mass spectrometer being used. For example, if equipment more sensitive were used, the amount of TBP can be decreased, e.g., by a factor of 10.

Figure 3:
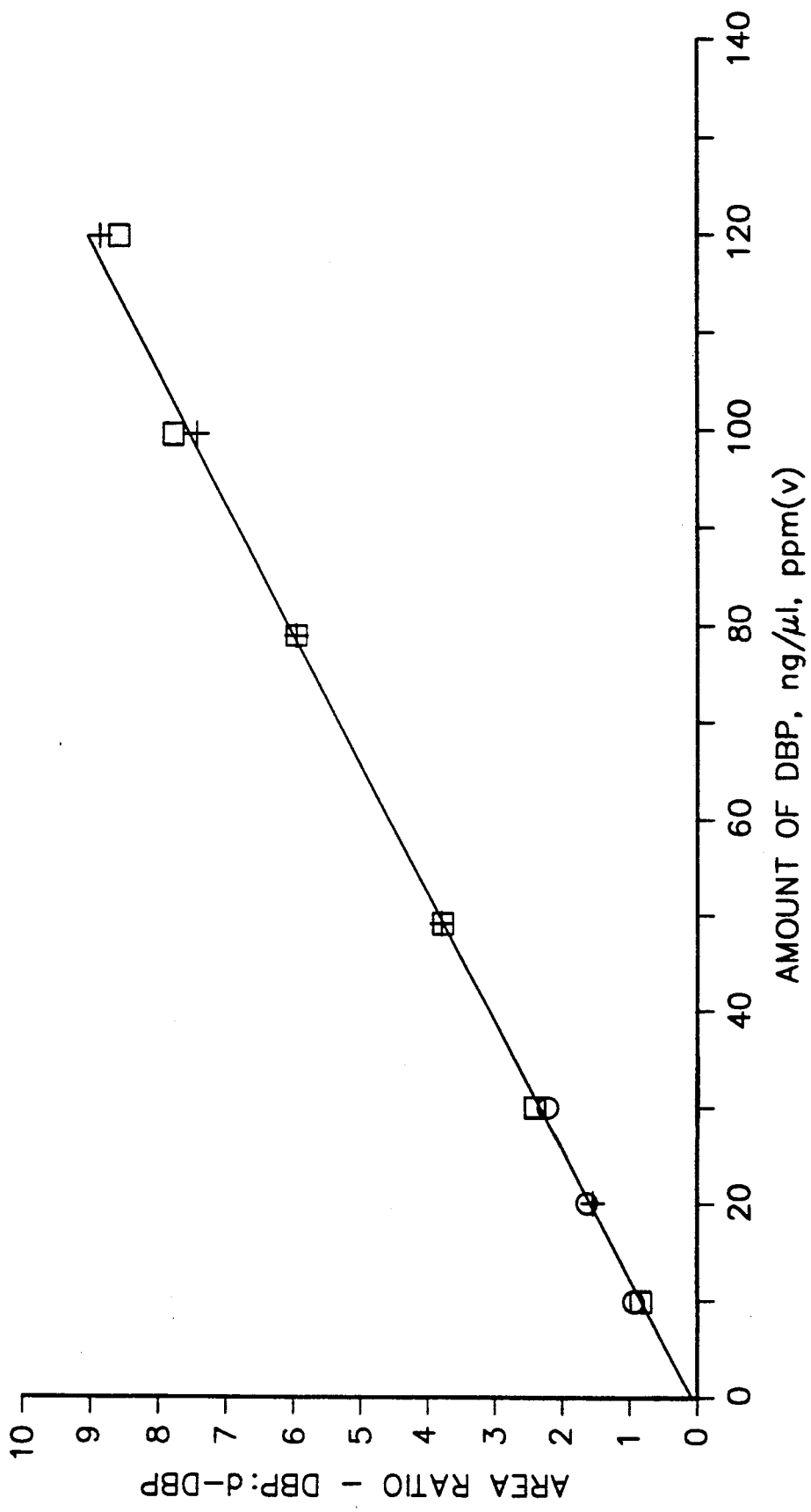
FIG. 3 is a graph showing a calibration plot for dibutyl phosphoric acid analysis obtained in accordance with the method of the invention.

The analytical method for calibrating the equipment will be described in detail with reference to the calibration plot of FIG. 3. Dibutyl phosphate, 97.6% by titration, is introduced in different volumes, together with the mass-labelled, fully deuterated dibutyl phosphate, to provide the calibration curve in FIG. 3. Two standard solutions, unlabelled O-standard and mass-labelled D-standard, are prepared according to the method outlined below.

An unlabelled solution of dibutyl phosphate (97.6%) is prepared in a solution of methylene chloride solvent at a concentration of about 0.1 mg/ml. The mass-labelled, deuterated dibutyl phosphate is combined with methylene chloride solvent at a concentration of 0.3 to 3.0 mg/ml. After preparing the O-standard and D-standard solutions, different volumes of the starting solution are prepared as shown in Table 1.

TABLE 1

| Vial No. | O-Standard (μl) | D-Standard (μl) |
|---|---|---|
| 1 | 10 | 10 |
| 2 | 30 | 10 |
| 3 | 50 | 10 |
| 4 | 80 | 10 |
| 5 | 100 | 10 |
| 6 | 120 | 10 |

The methylene chloride is evaporated and an excess of BSTFA is added at about 100 μl. Table 2 shows the resulting concentrations used for calibration.

TABLE 2

| Vial No. | DBP Concentration (ng/μl) | d-DBP Concentration (ng/μl) |
|---|---|---|
| 1 | 10 | 10 |
| 2 | 30 | 10 |
| 3 | 50 | 10 |
| 4 | 80 | 10 |
| 5 | 100 | 10 |
| 6 | 120 | 10 |

Because of the difficulty in resolving mass-labelled and unlabelled compounds chromatographically, the reconstructed ion chromatograms for DBP and d-DBP masses 171 and 174 are used for calibration. Masses 243 and 245 correspond to MBP and d-MBP.

The amount of DBP in a sample is determined from the ratio of the peak areas of DBP and d-DBP. Knowing the weight of the DBP in the sample and using the calibration curve of FIG. 3, the DBP concentration in the sample can be determined. Similarly, the concentration of MBP in a sample can be determined from the weight of MBP in the sample and a suitable calibration curve (see FIG. 2).

Four samples were prepared to compare the standard method of measurement involving diazomethane and GC with the analytical technique based on a deuterated internal standard. A known quantity of DBP and MBP was added to Sample Nos. 2 and 4. Sample Nos. 1 and 3 had unknown levels of contaminants. Table 3 compares the results of the respective methods.

TABLE 3

| Sample No. | Standard Method | | New Analytical Method | |
|---|---|---|---|---|
| | DBP (ppm) | MBP (ppm) | DBP (ppm) | MBP (ppm) |
| 1 | <5 | <5 | 7 | ND |
| | | | 7 | 0.2 |
| 2 | 90 | 120 | 94 | 112 |
| | | | 94 | 118 |
| | | | 99 | 118 |
| | | | 96 | 101 |
| | | | 90 | 94 |
| 3 | <5 | <5 | 7 | 0.3 |
| 4 | 100 | 110 | 98 | 132 |
| | | | 92 | 118 |

Good agreement is observed between the results for for the two techniques. Consequently, deuterated dibutyl and monobutyl phosphates are useful in providing a safe analytical method for determining the operating performance of a production solvent extraction system.

We claim:

1. A deuterated compound having the chemical formula $(C_4D_9O)PO_3H_2$.

2. A deuterated compound having the chemical formula $(C_4D_9O)_2PO_2H$.

* * * * *